(12) United States Patent
Wilde et al.

(10) Patent No.: US 7,641,409 B1
(45) Date of Patent: Jan. 5, 2010

(54) SINGLE-USE COSMETIC PACKAGE

(75) Inventors: Michele C. Wilde, New York, NY (US); Charles P. Neuner, Amityville, NY (US); George H. Kress, Fanwood, NJ (US)

(73) Assignee: ELC Management LLC, New York, NY (US)

( * ) Notice: Subject to any disclaimer, the term of this patent is extended or adjusted under 35 U.S.C. 154(b) by 0 days.

(21) Appl. No.: 12/469,747

(22) Filed: May 21, 2009

Related U.S. Application Data

(60) Provisional application No. 61/075,808, filed on Jun. 26, 2008.

(51) Int. Cl.
*B43K 5/14* (2006.01)

(52) U.S. Cl. .................. 401/132; 401/122; 401/126; 401/129; 206/209

(58) Field of Classification Search ......... 401/132–135, 401/121, 122, 125–130; 132/317; 206/209
See application file for complete search history.

(56) References Cited

U.S. PATENT DOCUMENTS

| | | | |
|---|---|---|---|
| 572,327 A | 12/1896 | Bryan | |
| 1,602,531 A * | 10/1926 | Itoh | ............ 132/308 |
| 2,547,779 A | 4/1951 | Renyck | |
| 2,814,420 A | 11/1957 | Elder, Jr., et al. | |
| 3,128,920 A | 4/1964 | Volckening et al. | |
| 3,204,835 A | 9/1965 | Michel | |
| 3,469,928 A | 9/1969 | Widegren | |
| 3,777,949 A | 12/1973 | Chiquiari-Arias | |
| 4,248,227 A | 2/1981 | Thomas | |
| 4,284,199 A | 8/1981 | Bigarella | |
| 4,711,354 A | 12/1987 | Bennett | |
| 4,732,287 A | 3/1988 | Bennett | |
| 4,786,534 A | 11/1988 | Aiken | |
| 4,889,228 A | 12/1989 | Gueret | |
| 4,952,204 A | 8/1990 | Korteweg | |
| 4,982,838 A | 1/1991 | Fitjer | |
| 5,320,217 A | 6/1994 | Lenarz | |
| 5,765,574 A | 6/1998 | Sheffler et al. | |
| 5,826,600 A | 10/1998 | Rowe et al. | |
| 5,862,818 A | 1/1999 | Marinelli | |
| 6,039,487 A | 3/2000 | Kristiansen | |
| 6,305,385 B1 | 10/2001 | Szekely | |
| 6,326,069 B1 | 12/2001 | Barnett et al. | |
| 6,516,947 B1 * | 2/2003 | Van Dyke et al. | ........... 206/361 |
| 6,572,296 B2 | 6/2003 | Schrepf | |

(Continued)

*Primary Examiner*—David J Walczak
(74) *Attorney, Agent, or Firm*—Martin W. Haerter

(57) ABSTRACT

A single-use cosmetic package has a pouch with a front wall and a back wall. A wand is stored in the pouch. Upper and lower seals hermetically seal the perimeter of the pouch. A middle seal divides the pouch into a product reservoir in a lower half of the pouch and a dry chamber in the upper half. The wand projects from a handle end in the dry chamber through the middle seal to an applicator end in the product reservoir. A dog-bone shaped sealing structure on the wand forms a hermetic seal with the middle seal. The dry chamber is opened by pulling opposite tabs to peel the front wall from the back wall. When the wand is pulled from the pouch, a flange on the wand expands the middle seal to form a wiper opening in the product reservoir. The wiper opening is sized to wipe the applicator end of the wand, or an applicator attached to the end of the wand.

9 Claims, 1 Drawing Sheet

U.S. PATENT DOCUMENTS

| | | | |
|---|---|---|---|
| 6,592,280 B2 * | 7/2003 | Petrich et al. | 401/126 |
| 6,685,013 B2 | 2/2004 | Discko, Jr. | |
| 6,709,181 B1 | 3/2004 | Montoli | |
| 7,008,133 B2 | 3/2006 | Ashe et al. | |
| 7,219,801 B2 | 5/2007 | Christian | |
| 7,223,035 B1 | 5/2007 | Engel | |
| 2006/0283728 A1 | 12/2006 | Patrick et al. | |

* cited by examiner

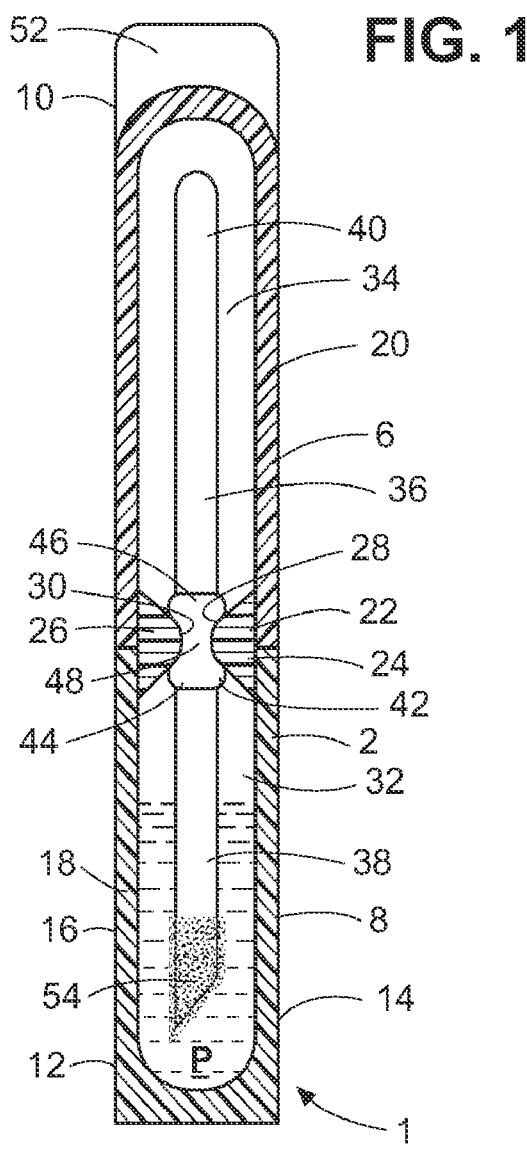
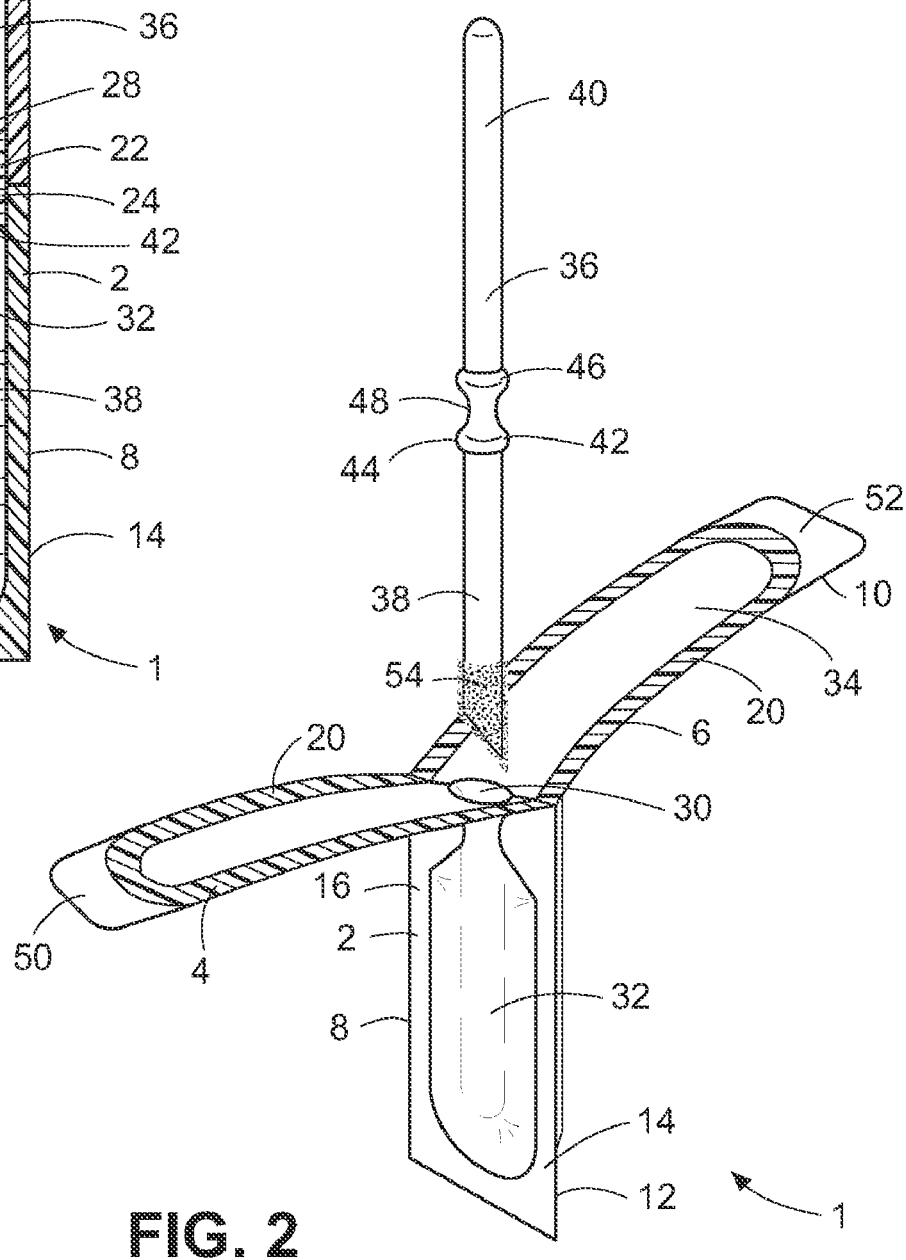

SINGLE-USE COSMETIC PACKAGE

CROSS-REFERENCE TO RELATED APPLICATIONS

This application claims priority of U.S. Provisional Patent Application Ser. No. 61/075,808 filed on Jun. 26, 2008.

BACKGROUND OF THE INVENTION

1. Field of the Invention

The present invention relates to cosmetic product packages, such as disposable cosmetic product sample packages, intended for single use. In particular, the present invention is directed to a cosmetic product package including a pouch, an applicator wand stored in the pouch, a peelable opening that provides access to the handle of the wand and a wiper opening for metering the dispensed sample.

2. Description of the Prior Art

Single-use containers serve at least two important roles in the cosmetic field, i.e., as unit-dose dispensers or as samplers. Unit-dose dispensers conveniently provide to the user a pre-measured amount of product, e.g., enough product for a single treatment or application. Samplers (sample size packages of product) are generally provided to consumers free of charge or at a nominal cost so that a consumer can experience a limited quantity of a product prior to making a purchase decision. With respect to samplers, it is important that the experience of sampling the product approximates the experience of using a saleable package (the package available for purchase). It is also advantageous if when used as a sampler the package is not readily usable multiple times. If a free sampler is reusable and/or contains too much product, there is significantly less incentive for a consumer to purchase a saleable package.

Present samplers are often smaller versions of saleable packages. For example, mascara product samplers are often reduced volume versions of the saleable package, complete with a saleable-type re-sealable container with a threaded neck and cap, a rod, a brush applicator and an elastomer wiper insert. The cost of such samplers is relatively high due to the quality and quality of parts (bottle, cap, rod, brush, wiper), complexity of structure, assembly and filling. In addition, because they can be resealed in an airtight fashion, the consumer can use such a sampler for several days or weeks, and thus has reduced incentive to purchase a corresponding saleable package.

Present pouch packages often have a separate neck member secured to the pouch. A wand is inserted through the neck member, which may include a wiper. See U.S. Pat. No. 5,862,818 to Marinelli. The separate neck member and/or wiper may add significantly to the cost of the package.

Alternative samplers may be made by blow molding, extrusion or vacuum forming less expensive bottles, squeeze tubes or blister packs, respectively. However, these less expensive alternatives often fail to provide a quality sampling experience that closely approximates the experience of using a saleable package.

U.S. Pat. Nos. 4,732,287 and 4,711,354 to Bennett, respectively, disclose cosmetic dispensers including an elongated hollow cylindrical container with an opening, and an elongated plastic article (applicator rod) provided in the container with an enlarged portion sealed or welded in the opening of the container. The basic dispenser requires at least two relatively costly components, the cylindrical container and the article (applicator rod), that are separately manufactured and subsequently assembled, thus increasing production cost.

U.S. Pat. No. 2,814,420 to Elder, Jr., et al. discloses a sealed package and container with a tubular body, a frusto-conical section extending into one end of the body and a stem joined by a breakable annular zone to the frusto-conical section. The body, frusto-conical section and stem are formed as a unitary part. The tubular body is squeezable to facilitate expelling product from the product reservoir. Accordingly, product could be inadvertently expelled during normal handling if the user inadvertently applies excessive pressure. To avoid this problem, the frusto-conical section is inverted by the user from a position extending into the body to a position extending outwardly from the body. While this feature would appear to reduce the incidence of inadvertent release of product, it may not totally eliminate the problem. In addition, the stem does not extend down below the frusto-conical section, so it appears that it would be difficult if not impossible for the stem to be dipped into the product in the container. It appears as if the stem, in order to be used as an applicator, would need to be loaded with product by squeezing product from tubular body.

U.S. Pat. No. 6,039,487 to Kristiansen discloses a disposable dispenser comprised of a tube extending from an upper end of a container. An open bottom end of the container is sealed after the container is charged with product. Prior to filling and sealing, an applicator rod is inserted into the tube, which is adapted to internally receive in friction fit the upper end of the applicator rod. The region where the tube and the neck of the container are joined is weakened so that the tube can be snapped away from the container. Again, the basic package requires at least two relatively costly components, the tube/container and the rod, which are separately manufactured and subsequently assembled.

U.S. Pat. No. 5,826,600 to Rowe et al. discloses a disposable dry-handle mascara applicator assembly. U.S. Pat. No. 4,952,204 to Kortweg discloses a dry handle swab assembly and unit. The containers disclosed in Rowe et al. and Kortweg are substantially the same as that disclosed in Kristiansen—a tube extending from an upper end of a container with an applicator rod secured in the tube. Each requires at least two relatively costly basic components, the tube/container and the rod.

U.S. Pat. No. 6,709,181 to Montoli discloses a mascara product sampler substantially similar in construction to a saleable package, i.e., complete with a re-sealable container with a threaded neck and cap, a rod, a brush applicator and an elastomer wiper insert. The relative complexity of the manufacturing and assembly is self-evident.

Accordingly, there is a need for a less complex single-use container constructed with relatively low cost components.

BRIEF SUMMARY OF THE INVENTION

It is an object of the invention to provide a single-use cosmetic product package that is simple in construction and has relatively low cost components. It is another object of the invention to provide a single-use cosmetic product package suitable for use as a sampler or as a unit-dose dispenser. It is yet another object of the invention to provide a basic single-use cosmetic product package whose function can be enhanced with the addition of conventional applicator heads, e.g., a twisted wire mascara brush. It is another object of the invention to provide a single-use cosmetic product package in the form of a pouch container having a product storage reservoir at one end and a dry chamber at the other end. A wiper opening defined by widened portions of the side seals provides a fluid communication channel between the reservoir and the chamber. A wand is stored in the pouch container with an applicator end in the reservoir, a handle end in the dry chamber and a sealing structure in the wiper opening such that it seals the wiper opening. A peelable seal allows separation of the portion of the pouch walls forming the dry chamber to provide access to the wand handle. It is another object of the invention to provide a single-use cosmetic product package that when used as a sampler delivers metered samples in a manner similar to a saleable container.

Accordingly, a single-use cosmetic product package is provided wherein the basic elements, a pouch container with a wiper opening formed by the pouch seams and a simple applicator wand, are minimal and low in cost.

The applicator end of the wand may be used as is, e.g., as a dipper to retrieve product, or the end may be enhanced with texture (e.g., grooves, ridges, bores, bumps) or a spatula-like flattened portion to enhance product loading and/or delivery of product. Alternatively, the applicator end may be enhanced by securing an applicator to it. For example, a sponge, a fibrous material, flocking or a brush may be secured to the applicator end to enhance loading and delivery of the product sample.

The pouch has a wiper opening formed between widened portions of the pouch side seals. The wiper is dimensioned to wipe excess product from the applicator end and/or applicator as it is drawn through the wiper. The opening is preferably dimensioned to approximate the size and function of the wiper in a corresponding saleable package for the same product.

The wand is provided with a sealing structure adapted to facilitate formation of a fluid tight seal about the wand when the wand is positioned within the pouch such that the applicator end is located in the product reservoir and the handle end is located in a dry chamber and the wiper opening is secured about the sealing structure of the wand in fluid tight contact to hermetically seal the product reservoir from the dry chamber.

Although the cosmetic container of the present invention is simple and low cost, it delivers metered amounts of cosmetic in a manner similar to more expensive saleable packages.

BRIEF DESCRIPTION OF THE DRAWINGS

FIG. 1 is a sectional view of the present invention showing the back wall of the pouch, the seals and the wand; and FIG. 2 is a front and left side perspective view showing the pouch in an open state with the wand withdrawn.

DETAILED DESCRIPTION OF THE INVENTION

Referring now to FIGS. 1-2, a single-use cosmetic product package is shown generally at reference number 1. The package comprises a pouch 2 having a front wall 4, a back wall 6 and a perimeter 8 defined by a top end 10, a bottom end 12, a first side edge 14 and a second side edge 16. At the bottom end of the pouch, the front wall 4 is secured to the back wall 6 by a lower seal 18 (indicated in FIG. 1 by diagonal cross-hatching) extending across the bottom end 12 and along a lower portion of each of the first side edge 14 and the second side edge 16. At the top end 10, the front wall 4 is secured to the back wall 6 by an upper seal 20 (indicated in FIGS. 1 and 2 by diagonal cross-hatching) extending across the top end 10 and along an upper portion of each of the first side edge 14 and the second side edge 16. The front wall 4 is further secured to the back wall 6 by a middle seal 22 (indicated in FIG. 1 by horizontal cross-hatching) having a first part 24 extending inwardly from the first side edge 14 toward a second part 26 extending inwardly from the second side edge 16, a gap 28 between the first part 24 and second part 26 of the middle seal 22 defines a wiper opening 30 adapted to meter product withdrawn from the package. The lower seal 18 and middle seal 22 define a product reservoir 32 between the front wall and the back wall at the bottom end of the pouch. The upper seal 20 and middle seal 22 defining a dry chamber 34 between the front wall and the back wall at the top end of the pouch. The lower seal 18, upper seal 20 and middle seal 22 hermetically seal the perimeter 8 of the pouch.

A wand 36 is provided in the pouch 2. The wand 36 has an applicator end 38 adapted to carry and deposit a cosmetic product P. Opposite the applicator end 38, a handle end 40 is provided that is adapted for grasping by a user. A sealing structure 42 is provided between the applicator end 38 and the handle end 40. The sealing structure 42 has an annular first flange 44 separated from an annular second flange 46 by an intermediate portion 48 that tapers from each of the first flange and the second flange to a reduced diameter between the first flange and the second flange. The sealing structure 42 is adapted to facilitate formation of a fluid tight seal about the wand between the wand and the pouch. Prior to forming the middle seal 22, the wand is positioned within the pouch such that the applicator end is located in the product reservoir 32 and the handle end is located in the dry chamber 34. Then the middle seal is formed such that the wiper opening 30 is secured about the sealing structure 42 of the wand in fluid tight contact to hermetically seal the product reservoir 32 from the dry chamber 34. The front wall 4 and back wall 6 are preferably not directly bonded to the wiper structure 42, but are in fluid tight contact with the sealing structure 42 due to the configuration of the sealing structure and the middle seal and due to the elasticity of the film or sheet material of the front wall and back wall. The diameter of the first flange and second flange is larger than that of the wand overall. The larger diameter of the flanges facilitates a tight seal about the sealing structure. The relatively rounded shape of each flange avoids tearing, cracking or piercing of the film that could be caused by a sharp edged structure. The tight seal prevents product P from leaking through the wiper opening to the dry chamber while the wand is secured in the opening. This keeps the handle end of the wand from being soiled with product.

The upper seal 20 of the pouch is peelable so that a user can separate a portion of the front wall 4 from the back wall 6 to open the dry chamber 34, grasp the handle end of the wand, and pull the applicator end of the wand through the wiper opening to withdraw a metered amount of a product from the product reservoir. A tab 50, an unsecured portion of the front wall, and an opposite tab 52, an unsecured portion of the back wall, each extend above the top seal 20 to facilitate opening the dry chamber 34. A user can grasp tabs 50 and 52 and pull them apart to separate the front wall from the back wall to open the dry chamber. The middle seal is significantly wider than the upper seal. The additional width of the middle seal resists peeling of the upper seal beyond the lower end of the dry chamber, and thus prevents the user from peeling the package open beyond the wiper opening.

The applicator end 38 of the wand may be used as is, e.g., as a dipper to retrieve product, or the end may be enhanced with texture (e.g., grooves, ridges, bores, bumps), flocking or a spatula-like flattened or cupped portion to enhance product loading and/or delivery of product. Alternatively, the applicator end 38 may be enhanced by securing an applicator 54 (indicated by stippling) to it. For example, a sponge, an elastic paddle, a fiber pad, flocking or a brush may be secured to the applicator end 38 to enhance loading and delivery of the product sample.

The annular first flange 44 is dimensioned to expand the wiper opening 30 when the wand 36 is withdrawn from the package 1. The wiper opening 30 expands from the reduced diameter of the intermediate portion 48 to a pre-selected size suitable for wiping the applicator end 38, or suitable for wiping an applicator 54 mounted on the applicator end 38. Expansion of the wiper opening is accomplished in part by releasing a small portion of each of the first part 24 and the second part 26 of the middle seal 22, i.e., the portion of each of the first part and second part of the middle seal that corresponds to the reduced diameter of the intermediate portion 48 of the sealing structure 42. Additionally, the sheet or film material of the front wall and back wall may stretch and expand, or have sufficient elasticity to permit the first flange to be withdrawn.

The front wall 4 and back wall 6 are made of any sheet material suitable for use in a sampler pouch, so long as the material is compatible with the cosmetic product to be stored. For example, the sheet material may be comprised of successive layers of coex (for example, co-extruded poly propylene or poly ester), adhesive, aluminum foil, adhesive and polymeric material (for example, poly propylene or polyester). The lower seal 18, upper seal 20 and middle seal 22 are formed by a suitable adhesive that is compatible with the sheet material and the cosmetic product to be stored therein, and is peelable upon curing. Alternatively, the film may be selected to be capable of bonding to itself to form a hermetic seal without the need for adhesive, but still exhibit the desired peelability. Examples of suitable self-bonding film layer materials, such as acrylonitrile methylacrylate, are disclosed in U.S. Pat. No. 4,786,534 to Aiken, incorporated herein by reference in its entirety. The lower seal, upper seal and middle seal are formed by heat sealing or, optionally, induction sealing, sonic welding, etc.

The wand 36 is molded in a single integral piece that includes the applicator end 38, handle end 40 and sealing structure 42. The wand 36 is molded from a suitable plastic material such as hytrel, poly propylene, polyester or other polymeric material that is compatible with cosmetic product. Preferably, the material is also selected to facilitate bonding of, for example, flocking fibers or a sponge material to the applicator end 38. The configuration of the applicator end is selected to facilitate application of the cosmetic product to be stored.

Once the wand 36 has been molded, it is placed between a pre-cut front wall and back wall and at least the upper seal, the middle seal and portions of the lower seal along the first side edge and second side edge are formed by heat sealing, sonic welding, induction sealing, adhesive or other suitable means. At least a portion of the lower seal along the bottom end is left un-bonded to provide access to the product reservoir for filling product. The un-bonded bottom end seal may also provide access to the product reservoir so that an applicator 54 can be secured on the applicator end 38. Once the applicator 54 is installed (optional) on the applicator end 38, and once the product P has been loaded into the product reservoir, the un-bonded portion of the lower seal at the bottom end may be sealed by heat sealing, sonic welding, induction sealing, adhesive or other suitable means.

The package is particularly useful as a single use container, e.g., a sampler or a unit dose package. The pouch may be used as a sampler at a retail counter, a giveaway with counter promotions, a saleable "grab bag" item, in magazines and mailers, and in other ways. The package is suitable for use with, for example, mascara, eyelash, eye shadow and other eye products, nail polish, nail care products, lipstick, lip gloss, lip color, lip balm, lotions, serums, treatment products, sun block, make-up, foundations, concealers, depilatories and other treatment and make-up products. The applicator end or applicator can be selected to accommodate use with a particular product from the list above.

The middle seal forms a hermetic seal about the sealing structure of the wand and forms a wiper opening in the pouch when the wand is withdrawn from the pouch. This eliminates the need for a separate wiper component, thus reducing the cost of the package substantially while maintaining a user experience that is similar to a salable package.

It is understood that various modifications and changes in the specific form and construction of the various parts can be made without departing from the scope of the following claims.

What is claimed is:

1. A single-use cosmetic product package comprising:
    a pouch having a front wall, a back wall and a perimeter defined by a top end, a bottom end, a first side edge and a second side edge, the front wall secured to the back wall by a lower seal extending across the bottom end and along a lower portion of each of the first side edge and the second side edge, an upper seal extending across the top end and along an upper portion of each of the first side edge and the second side edge, and a middle seal having a first part extending inwardly from the first side edge toward a second part extending inwardly from the second side edge, a gap between the first part and second part defining a wiper opening adapted to meter product withdrawn from the package, the lower seal and middle seal defining a product reservoir between the front wall and the back wall at the bottom end of the pouch, and the upper seal and middle seal defining a dry chamber between the front wall and the back wall at the top end of the pouch, the lower seal, upper seal and middle seal hermetically sealing the perimeter of the pouch; and
    a wand in the pouch, the wand having an applicator end adapted to carry and deposit a cosmetic product, a handle end opposite the applicator end, and a sealing structure between the applicator end and the handle end, the sealing structure having an annular first flange separated from an annular second flange by an intermediate portion that tapers from each of the first flange and the second flange to a reduced diameter between the first flange and the second flange, the sealing structure adapted to facilitate formation of a fluid tight seal about the wand, the wand positioned within the pouch such that the applicator end is located in the product reservoir, the handle end is located in the dry chamber and the wiper opening is secured about the sealing structure of the wand in fluid tight contact to hermetically seal the product reservoir from the dry chamber; wherein
    the upper seal of the pouch is peelable so that a user can separate a portion of the front wall and back wall to open the dry chamber, grasp the handle end of the wand, and pull the applicator end of the wand through the wiper opening to withdraw a metered amount of a product from the product reservoir.

2. The single-use cosmetic product package of claim 1 further comprising an unsecured portion of the front wall and an opposite unsecured portion of the back wall each extending above the top seal to facilitate opening the dry chamber.

3. The single-use cosmetic product package of claim 1 further comprising an applicator secured to the applicator end of the wand.

4. The single-use cosmetic product package of claim 3 wherein the annular first flange is dimensioned to expand the wiper opening when the wand is withdrawn from the package from the reduced diameter between the first flange and the second flange to a pre-selected size suitable for wiping the applicator.

5. The single-use cosmetic product package of claim 3 wherein the applicator is selected from one of a brush, a fiber pad, a sponge or a paddle.

6. The single-use cosmetic product package of claim 1 wherein the annular first flange is dimensioned to expand the wiper opening when the wand is withdrawn from the package from the reduced diameter between the first flange and the second flange to a pre-selected size suitable for wiping the applicator end.

7. The single-use cosmetic product package of claim 1 wherein the applicator end further comprises a spatula.

8. The single-use cosmetic product package of claim 1 further comprising flocked fiber secured to the applicator end.

9. The single-use cosmetic product package of claim 1 further comprising texture on the applicator end selected from grooves, ridges, bores or bumps adapted to enhance at least one of product loading or product distribution.

* * * * *